United States Patent [19]

Broughton

[11] 4,277,249
[45] Jul. 7, 1981

[54] MAMMALIAN SOMATOMEDIN MEASUREMENT

[75] Inventor: Alan Broughton, Laguna Niguel, Calif.

[73] Assignee: Nichols Institute, San Pedro, Calif.

[21] Appl. No.: 84,800

[22] Filed: Oct. 15, 1979

[51] Int. Cl.³ .............................................. G01N 33/74
[52] U.S. Cl. ........................................ 23/230 B; 435/5; 435/7
[58] Field of Search ..................... 23/230 B; 435/7, 5

[56] References Cited

PUBLICATIONS

Richard W. Furlanetto et al., The Journal of Clinical Investigation, vol. 60, pp. 648–657, 1977.
S. L. Blethen et al., Proceedings of the Endocrine Society, 61st Annual Meeting, Abstract 592, Jun. 13–15, 1979.
Chemical Abstracts, vol. 84, 161310a, 1976.
Chemical Abstracts, vol. 92, 106023z, 1980.

*Primary Examiner*—Robert J. Warden
*Attorney, Agent, or Firm*—Lyon & Lyon

[57] ABSTRACT

Methods and means for collection of blood samples for Somatomedin assay, while suppressing exogenous Somatomedin generation, wherein a Somatomedin-containing blood specimen is absorbed on an absorbent medium and air-dried at ambient temperature, whereafter a portion of the blood-smear containing medium of predetermined uniform dimensions is removed and the Somatomedin activity therein eluted for assay.

7 Claims, 5 Drawing Figures

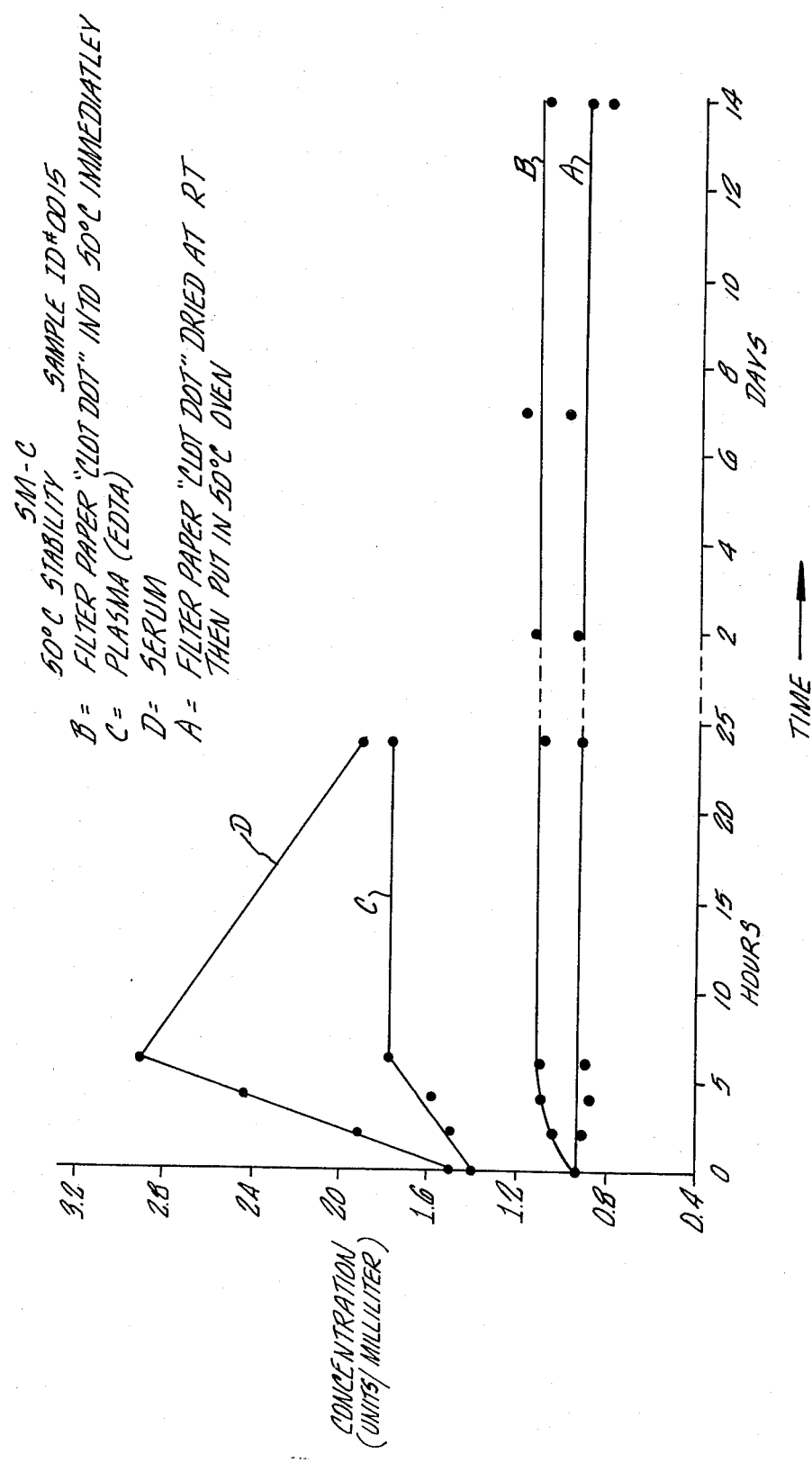

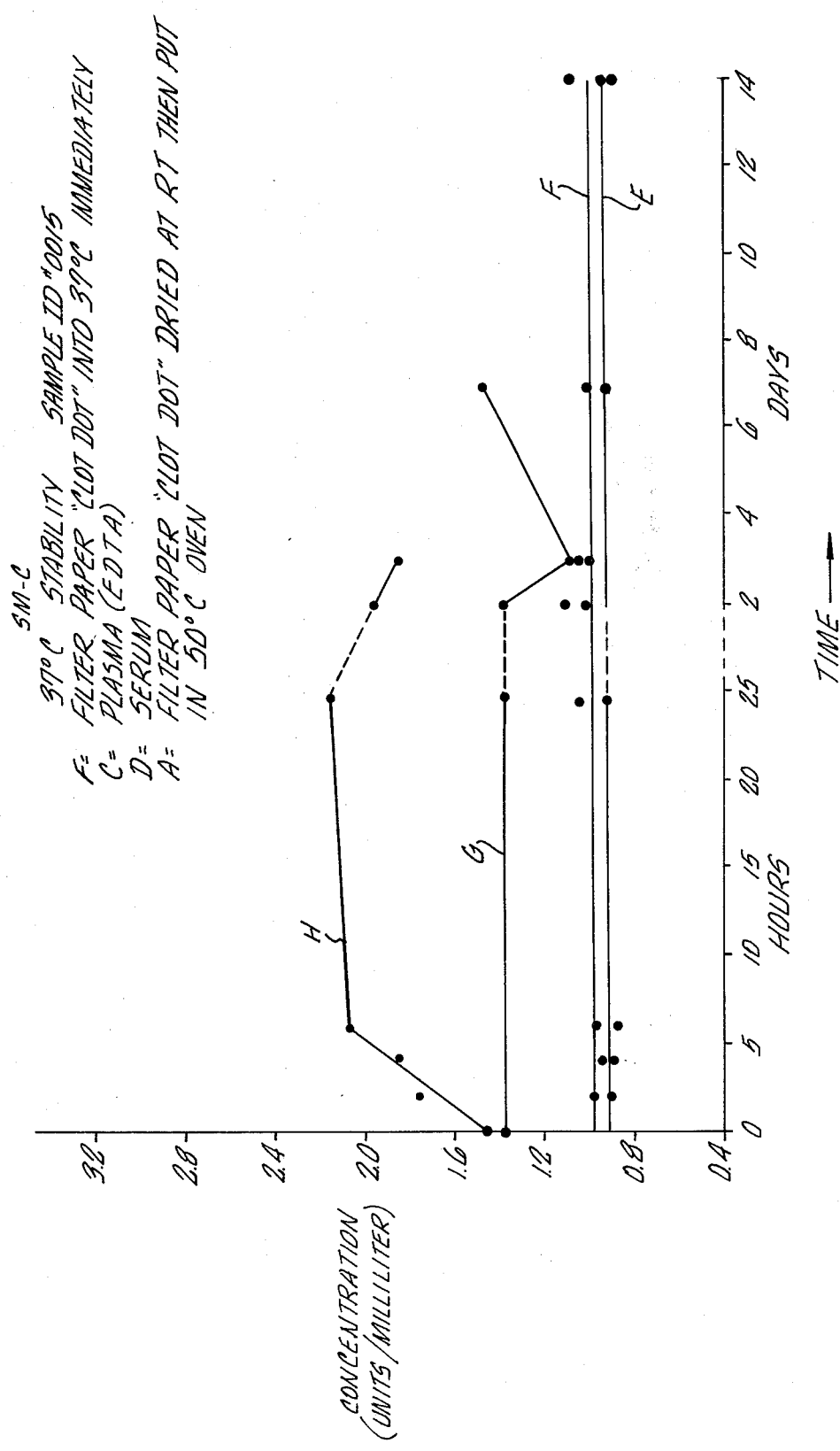

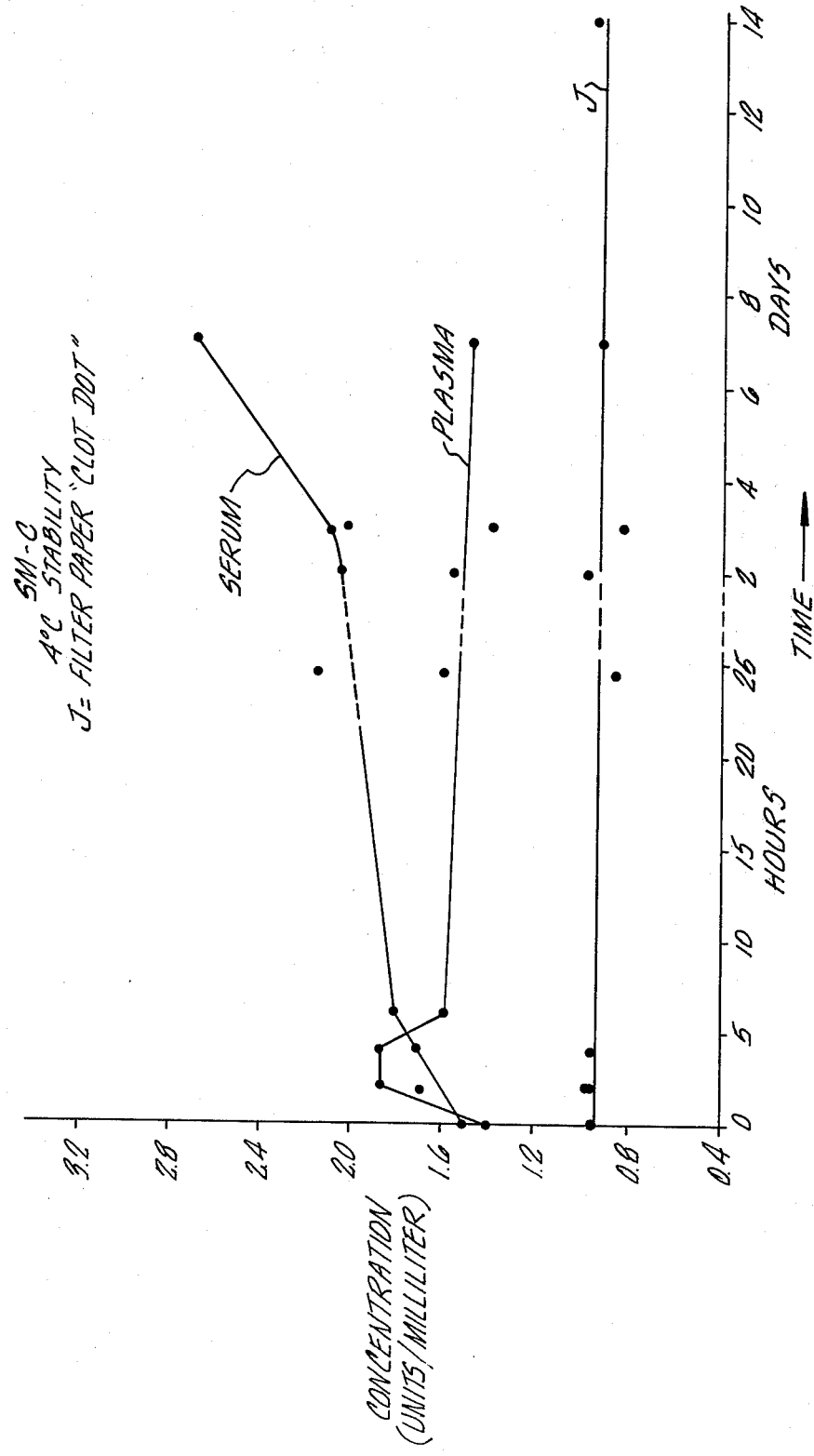

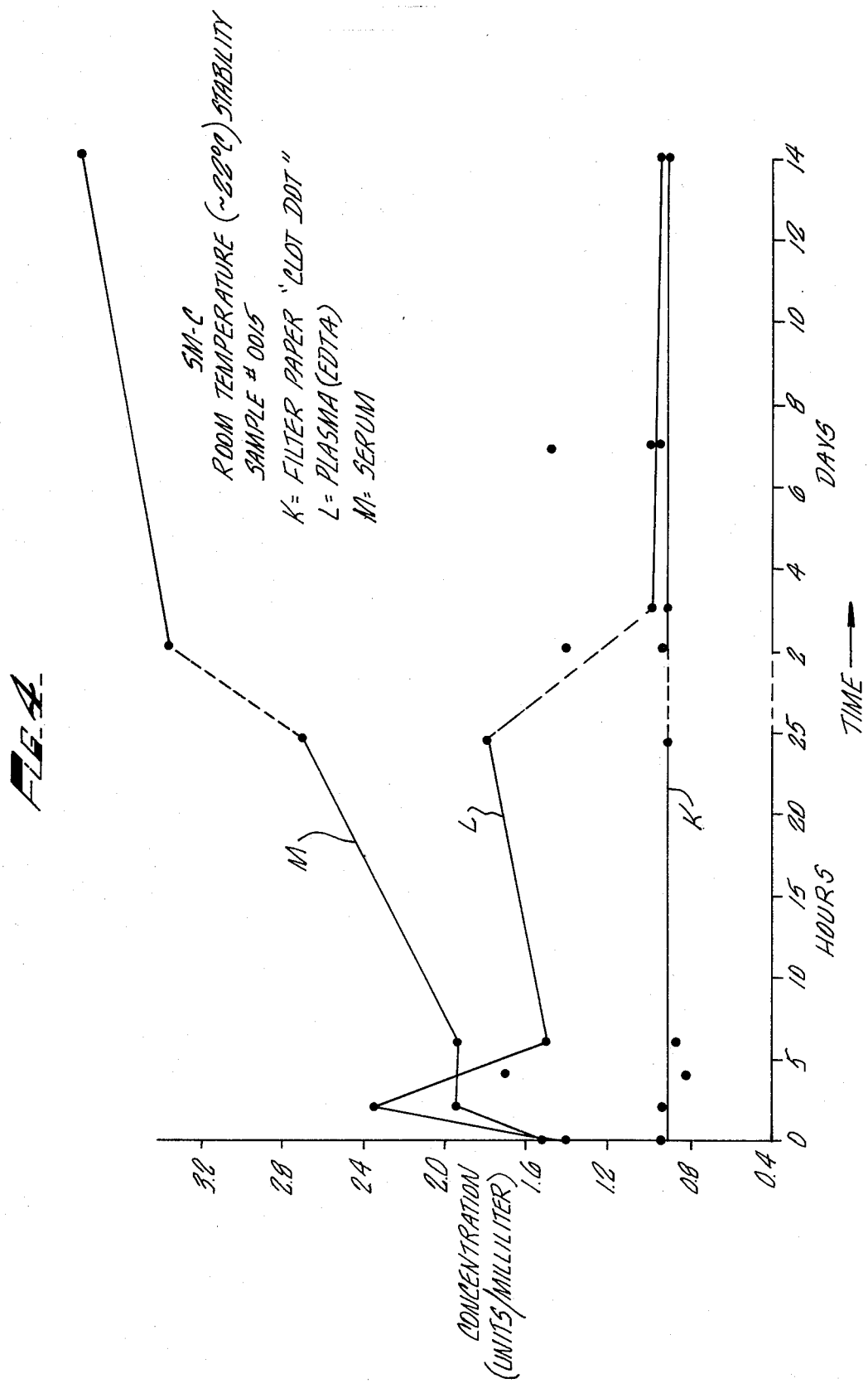

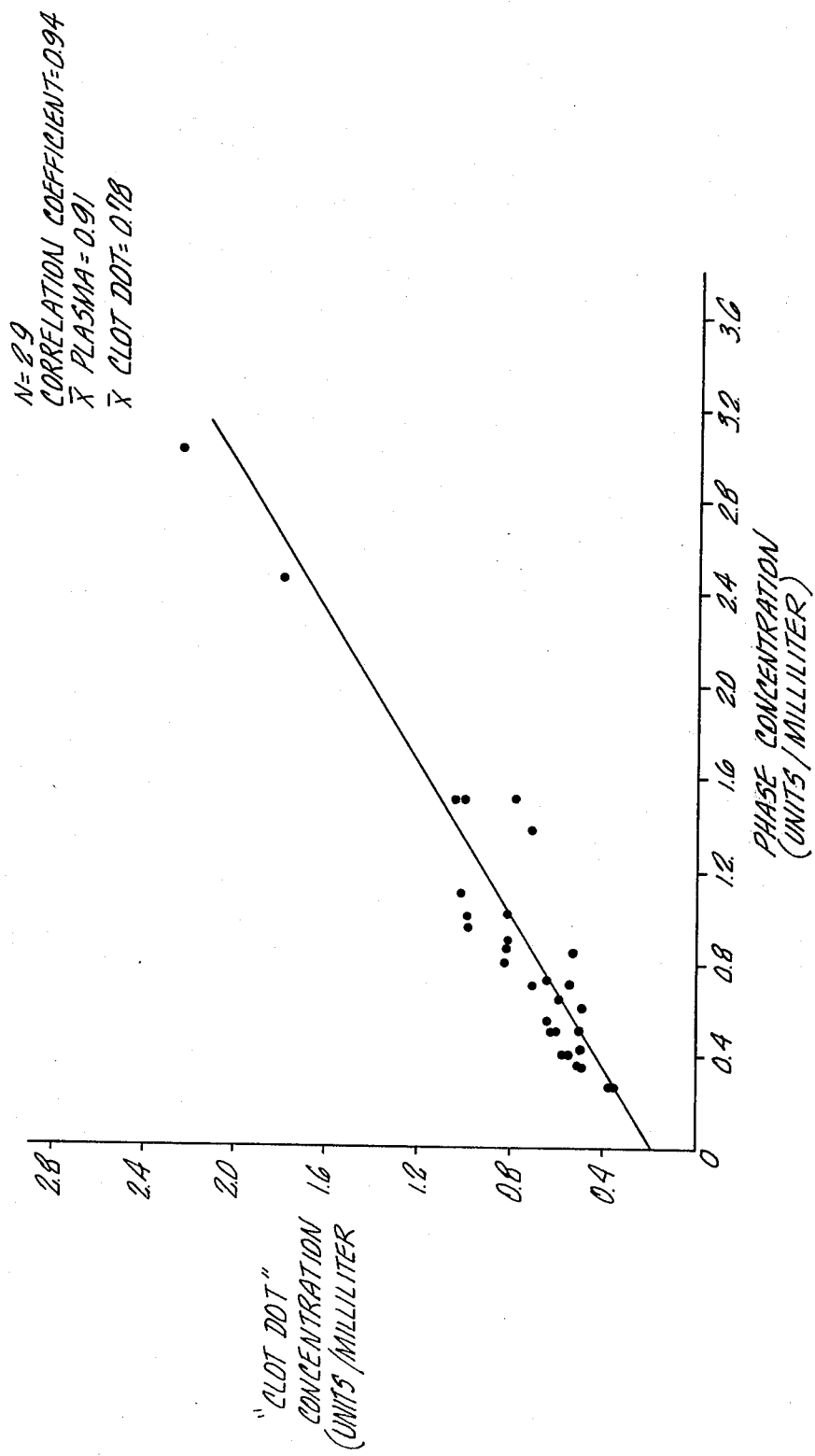

MAMMALIAN SOMATOMEDIN MEASUREMENT

BACKGROUND OF THE INVENTION

Human growth hormone (HGH) is a species-specific polypeptide hormone secreted by the pituitary. It is directly implicated in various anti-insulin actions, and indirectly involved in the promotion of growth. Its activity in the latter regard has led to assay of sera for HGH content as an aid in the diagnosis of such diseases as hypopituitary dwarfism (human growth hormone insufficiency) and the form of giganticism known as acromegaly (human growth hormone excess). The use of HGH assay in large-scale screening of potentially afflicted subjects has heretofore been problematic, owing to the fact that HGH levels in the blood are variable, even in normal subjects, as a function of food intake, exercise, and the like. Before reliable diagnosis can be made, it has been necessary in most instances to repeat assays.

The Somatomedins are proteins, probably generated in the liver, and possibly in other organs, as a result of the influence of HGH. In turn, these stimulate increased protein synthesis, cell proliferation and chondrogenesis, the latter leading to increased skeletal growth. Unlike HGH, the blood levels of the Somatomedins are relatively constant, permitting one-time assay for diagnosis. Somatomedin-C is one of a larger group of Somatomedin proteins. Its blood level is regulated by HGH. Somatomedin-C concentrations have been found to correlate well with HGH deficient and HGH excessive humans by radioimmunoassay, when compared to normal populations. Furlanetto, R. W., et al., *J. Clin. Invest.*, 60: 648, 1977. All references cited heretofore and hereafter are incorporated by reference into this application to illuminate the background of the invention.

Because of the relative constancy of Somatomedin-C levels in blood count specimens, blood may be drawn at any time of day, unaffected by food intake and without necessary resort to exercise or other stimulation. Heretofore, to obtain samples for Somatomedin-C assay, it has been necessary to draw on the order of five milliliters of blood, prevent clotting by the addition of Ethylene Diamine Tetraacetate (EDTA), then separate plasma, which is next frozen for shipment to the reference laboratory where the assay is to be conducted. If blood is collected for serum, it must be chilled immediately, centrifuged at low temperature, and kept frozen until the time of assay.

Aside from the general inconvenience of drawing a large blood sample (particularly from children), certain peculiar properties of Somatomedin-C have prevented entirely accurate and efficient assays of Somatomedin-C. Somatomedin-C is "generated" in extracted serum and plasma in a temperature, time, pH and divalent cation dependent process. Blethen, S. L., et al., *Proceedings of The Endocrine Society*, 61st Annual Meeting, Abstract 592, June 13–15, 1979. The immunoreactive Somatomedin-C concentration in serum may increase as much as three-fold, merely upon standing at room temperature. This can lead to a serious lack of uniformity in collecting and storing sera for purpose of Somatomedin assay. This phenomenon is hereafter referred to as the "exogenous generation" of Somatomedin-C, and is believed to be the result of an enzymatic process acting on a serum macromolecule. Were a chilled blood sample, drawn from a normal patient, to thaw well before assay, inordinately high levels of Somatomedin-C might be found, leading to an incorrect diagnosis of acromegaly. Alternatively, were the same thing to happen in the case of a sample drawn from a subject suffering from undiagnosed hypopituitary dwarfism, the assay of Somatomedin-C might indicate normal levels, owing to Somatomedin generation in the sample following its collection. This problem has led leading workers in the field to suggest that "serum Somatomedin assays may yield anomalous results unless conditions of collection and storage are rigorously standardized". *Proceedings*, supra.

A need accordingly has existed for methods and means of Somatomedin assay, unattended by the twofold problems that have characterized past practice: extraction and storage of large volumes of blood, and the relative unreliability of serum assays and resultant occasions for misdiagnosis of HGH content in human patients.

SUMMARY OF THE INVENTION

It has now been discovered that the problems which have arisen in Somatomedin-C assay in the past can be solved, and the procedure at the same time greatly simplified, not by 'rigorous standardization' of assay procedure, but instead by expedients which are simple in the extreme and admit of wide variation in sample collection procedures. It has been found that whole blood samples in merely microliter quantity can be absorbed on filter paper at the collection point, dried, and the blood eluted for immunoassay from a portion of the filter paper of predetermined size, e.g., simply by punching out a paper "dot" from the blood smear on the paper. In addition to substantially decreasing the quantity of blood required and the concomitant need for venipuncture, the invention eliminates the necessity of freezing samples prior to assay with the attendant danger that the generation phenomenon will lead to improper diagnoses. Instead, samples can simply be taken, dried on the paper, and mailed to a central reference laboratory for immunoassay.

The manner in which these and other objects and advantages of the invention may be obtained appears further from the detailed description which follows and from the accompanying drawings in which:

FIG. 1 is a graph of the concentration of Somatomedin-C versus time, determined by immunoassay of four different types of blood preparation incubated at 50° C.;

FIG. 2 is a graph of the concentration of Somatomedin-C versus time, determined by immunoassay of four different types of blood preparation incubated at 37° C.;

FIG. 3 is a graph of the concentration of Somatomedin-C versus time, determined by immunoassay of three different types of blood preparation chilled at 4° C.;

FIG. 4 is a graph of the concentration of Somatomedin-C versus time, determined by immunoassay of three different types of blood preparation at room temperature; and FIG. 5 is a graph of the concentration of Somatomedin-C, determined by the immunoassay of a filter paper preparation, as a function of the concentration of Somatomedin-C, determined by immunoassay of EDTA-plasma from the same blood source.

DETAILED DESCRIPTION OF THE INVENTION

This invention provides methods for determining the concentration of Somatomedin-C while suppressing exogenous generation of Somatomedin-C after the collection of biological fluid containing Somatomedin-C, by absorption of the fluid on an absorbent medium, drying the medium after absorbing the fluid, eluting the fluid from a portion of the absorbing medium, and determining the activity of the eluate's Somatomedin-C by assay.

The most preferred technique requires collection of no more than about 5 microliters of blood. This need not be done by venipuncture, but may instead involve simple subcutaneous puncture of dermal capillaries by any appropriate implement. The blood is allowed to flow freely from the puncture onto an absorbent medium, most preferably Specimen Collection Paper 903, Schleicher & Schuell. This eliminates the need for the extraction of a large quantity of blood and the cumbersome means for storage of the collected blood prior to assay.

After the absorption is complete, the filter paper is simply dried, most preferably by air and at room temperature. Immediate air drying at room temperature, prior to incubation, suppresses exogeneous generation of Somatomedin-C. The collection of blood as either plasma or serum, under methods heretofore used and described, has resulted in significant exogenous generation of Somatomedin-C, particularly over the first five to ten hours after collection. The air drying technique essentially eliminates this generation phenomenon.

After the filter paper is sufficiently dried, the most preferred technique is for portions of the filter paper to be punched out, resulting in punched out paper "dots" of uniform size and dimension. This allows the concentration of Somatomedin-C in the paper dot unknowns to be compared to concentrations of Somatomedin-C in a "standard" Somatomedin-C blood composition "dot" of the same dimension, containing an equivalent volume of absorbed blood. The standard "dot" can be prepared from an appropriate subject which subject is circumscribed by preselected parameters, e.g., a fasting human male between ages 30–35 and having a Somatomedin-C concentration within a normal range.

The invention is further illustrated and compared to prior means of Somatomedin assay in the Examples of preferred embodiments which follow.

EXAMPLES

Materials and Methods

Somatomedin-C stability and the "generation" phenomenon were analyzed by various preparational techniques. Freshly drawn blood was collected from a non-fasting normal male subject. Two types of samples were collected: Red-Top vacutainer tubes (clot tube) of serum, and purple-top vacutainer tubes of plasma-EDTA. All of these tubes were immediately submerged in ice.

Three types of preparations were made from the collected samples: filter paper blood spots (dots), serum, and EDTA plasma. The filter paper blood spots were made as follows. Immediately after collection, blood was taken from the chilled red-top vacutainer. Using a Pasteur pipette, this blood was spotted on filter paper SS 903, approximately one drop of blood per spot. The filter paper blood dots were dried and then incubated under the following varying conditions:

(a) dried for two hours at room temperature (22° C.), then incubated at room temperature;

(b) dried for two hours at room temperature, then incubated at 4° C.;

(c) dried for two hours at room temperature, then incubated at 37° C.;

(d) dried at 37° C. and incubated at 37° C.;

(e) dried at room temperature for two hours, then incubated at 50° C.;

(f) dried at 50° C., then incubated at 50° C.

At designated times (1 hr., 2 hrs., 2 days, etc.) measured after collection of the blood and during either the drying or incubation phases of the filter paper, dots one-eighth of an inch in diameter were punched out of the filter paper and stored in glass dispensing radioimmunoassay tubes (10 millimeters × 75 millimeters) at −20° C. until the time of assays.

The serum preparations were made from the red-top vacutainer samples after they had clotted at room temperature for 45 minutes and had been centrifuged at 4° C. for ten minutes. Separate aliquots of serum were then incubated at the following temperatures:

(a) at room temperature (22° C.);

(b) at 4° C.;

(c) at 37° C.;

(d) at 50° C.

At the same designated times (1 hr. 2 hrs., etc.) after collection of the serum and during the incubation of the serum aliquots, further smaller aliquots were taken and stored at −20° C. until the radioimmunoassays were performed.

The EDTA Plasma preparations were made from the EDTA purple-top vacutainer samples, and centrifuged at 4° C. for ten minutes. Separate aliquots of plasma were then incubated at the following temperatures:

(a) at room temperature (22° C.);

(b) at 4° C.;

(c) at 37° C.;

(d) at 50° C.

Again at the same discrete times after collection of the plasma and during the incubation of the plasma aliquots, further smaller aliquots were taken and stored at −20° C. until the radioimmunoassays were performed.

After the above described preparations, the serum and plasma aliquots were ready for radioimmunoassay by the method of Furlanetto, supra. To prepare the blood absorbed in the filter paper dots, there had to be an elution of the absorbed blood first however. In performing the radioimmunoassays antibodies to Somatomedin-C were prepared by the methods further described in Furlanetto.

Somatomedin-C concentrations' measurements are made in "units per milliliter"; a unit of Somatomedin-C is defined as the quantity of Somatomedin-C in one milliliter of pooled serum from normal adult male subjects. Since blood collection and storage techniques vary, a "unit" of Somatomedin-c might commensurately vary.

Each of the above described preparations has a "baseline" or standard value for concentration of Somatomedin-C. The filter paper dots have a baseline value determined after drying of the dots for two hours and prior to incubation. The baseline values for the serum aliquot preparations were determined on the aliquots after clotting and centrifugation had occurred and before incubation. The plasma aliquot preparations had baseline values determined after centrifugation and prior to any incubation.

EXAMPLE 1

FIG. 1 demonstrates the comparative measurements of the concentration of Somatomedin-C in units/milliliter at 50° C. of the various species (filter paper, serum, plasma) of one subject's blood, dried and/or incubated in differing fashion. Line A shows concentrations in filter paper dots, dried at room temperature, and then incubated at 50° C. Line A is a horizontal line with a slope of O. The concentration of Somatomedin-C, as a function of time after collection from the male subject, is shown to be constant. Line B is a graph of the measurements of the concentration of Somatomedin-C, versus time after collection on the filter paper, which paper is placed immediately into a 50° C. incubator, and not previously dried at room temperature. Line B demonstrates that there is a generation of Somatomedin-C within the first five hours after the collection of blood from the male subject. This is believed to show that there is an exogenous increase in the concentration of Somatomedin-C, and a misleading indicator of the endogenous concentration of Somatomedin-C in the subject. Line C shows the concentration of Somatomedin-C in the EDTA plasma incubated at 50° C. It shows a baseline concentration of Somatomedin-C of 1.4 units/milliliter at time zero whereas lines A and B demonstrate baseline concentrations of less than 0.9 units/milliliter at time zero. This difference between the two baseline concentrations reflects the rapidity of generation of Somatomedin-C during the first few minutes after collection and during centrifugation. Line C again demonstrates the exogenous generation of Somatomedin-C in the first five plus hours of incubation at 50° C. This generation provides a misleading indicator of the endogenous or natural concentration of Somatomedin-C. Line D shows the concentration of Somatomedin-C in blood serum of the male subject. Within the first six hours after collection of the serum, the generation phenomenon results in an approximate doubling of the endogenous concentration of Somatomedin-C, as measured by the baseline value.

FIG. 1 demonstrates vis-a-vis this experiment that the method of preparation of Somatomedin-C for assay has great consequences as to the reliability of the results. The filter paper method, including the drying at room temperature for two hours and then incubating at 50° C. demonstrates a constancy throughout time (line A). All other methods are more or less misleading, and would indicate more Somatomedin-C in the subject than is endogenous to that subject. These misleading methods could result in a misdiagnosis.

EXAMPLE 2

FIG. 2 graphs the measurements of the concentration of Somatomedin-C in each of the preparations (filter paper, serum, plasma), as a function of time after collection, and incubated at 37° C. Line E graphs measurements in blood prepared as a filter paper dot, dried at room temperature, and then incubated at 37° C. Line E shows that the results of measuring the concentration of Somatomedin-C in units/millimeters do not vary over time of incubation, when incubation is preceded by drying at room temperature for two hours. The concentration is constant. Line F demonstrates that the placing of the filter paper dot into the 37° C. incubator immediately after its preparation, without any amount of significant air drying, results in a constant measurement of Somatomedin-C concentration as a function of time. Line G shows the concentrations of Somatomedin-C in plasma which is incubated at 37° C., immediately after centrifugation of the plasma. There is a constancy of concentrations throughout time, however, the EDTA plasma has a greater baseline value (1.4) at time zero than the filter paper species (0.96). This reflects the rapidity of the generation phenomenon after the collection of the blood and the necessity of immediate suppression of that phenomenon. Line H shows the concentration of Somatomedin-C in serum incubated at 37° C. immediately after centrifugation. It shows a generation of Somatomedin-C during the first six hours of incubation without preliminarily air drying on filter paper. This could mislead an investigator as to the endogenous concentration of Somatomedin-C in the subject.

Example 2 demonstrates that the use of the clot drying technique, followed by incubation, is a reliable indicator of the true concentration of Somatomedin-C in the subject.

EXAMPLE 3

FIG. 3 graphs the measurements of the concentrations of Somatomedin-C in each of three species of blood preparations (filter paper, plasma, serum), as a function of time after collection and incubated at 4° C. Line J shows the same linearity described in both Examples 1 and 2 for the measurements of concentrations of Somatomedin-C in the filter paper clot dot. Again the air drying of the filter paper prior to incubation suppresses exogenous generation of Somatomedin-C after collection of the blood.

EXAMPLE 4

FIG. 4 shows that the concentration of Somatomedin-C is constant if the blood is prepared by absorption on filter paper, and dried at room temperature, before incubation at room temperature (Line K). The EDTA plasma species and the serum species show significantly increased baseline levels, as well as gross generation in the first few hours after collection (Lines L and M respectively). Again this could result in misdiagnosis of the endogenous concentration of Somatomedin-C in the subject.

That the clot dot method is more reliable than the traditional EDTA-plasma and serum methods of preparing blood for immunoassay of the Somatomedin-C concentration appears from Table 1 below. In the same number (29) of observations in the same subjects, there was a correlation co-efficient of 0.9 between the plasma Somatomedin-C concentration and the human subjects' correlative "clot dot" concentration (FIG. 5). The standard deviation in the "clot dot" preparations was 0.40 versus a 0.63 standard deviation in the plasma measurements of Somatomedin-C concentration. This smaller deviation in the clot dot preparations demonstrates the lower risk of generation of Somatomedin-C, more consistency in measurement, and more precision in the clot dot technique, than in the traditional plasma measurement technique.

TABLE 1

| Plasma SM-C vs. "Clot Dot" SM-C | | | | | |
|---|---|---|---|---|---|
| ID# | Plasma U/ml | "Clot Dot" U/ml | ID# | Plasma U/ml | "Clot Dot" U/ml |
| 0011 | 0.84 | 0.53 | 0150 | 1.54 | 1.08 |
| 0012 | 0.51 | 0.60 | 0156 | 0.80 | 0.82 |
| 0017 | 0.50 | 0.50 | 0158 | 0.71 | 0.69 |

TABLE 1-continued

| Plasma SM-C vs. "Clot Dot" SM-C | | | | | |
|---|---|---|---|---|---|
| 0020 | 0.61 | 0.51 | 0160 | 3.0 | 2.25 |
| 0037 | 0.55 | 0.64 | 0162 | 1.0 | 0.96 |
| 0042 | 1.06 | 0.82 | 0248 | 0.4 | 0.57 |
| 0044 | 0.90 | 0.81 | 0249 | 1.49 | 0.76 |
| 0097 | 0.42 | 0.50 | 0258 | 1.09 | 1.03 |
| 0101 | 0.26 | 0.39 | 0261 | 1.37 | 0.72 |
| 0104 | 1.57 | 0.94 | 0264 | 0.71 | 0.55 |
| 0112 | 0.64 | 0.60 | 0267 | 0.40 | 0.56 |
| 0117 | 0.95 | 0.98 | 0269 | 0.86 | 0.82 |
| 0129 | 0.72 | 0.64 | 0270 | 0.35 | 0.51 |
| 0134 | 2.45 | 1.84 | 0272 | 0.25 | 0.36 |
| 0136 | 0.58 | 0.62 | | | |

| | Plasma | "Clot Dot" |
|---|---|---|
| Number of observations | 29 | 29 |
| Mean | 0.91 | 0.78 |
| Std. Deviation | 0.63 | 0.40 |
| Low Value | 0.25 | 0.36 |
| High Value | 3.0 | 2.25 |

Table 2 below confirms that in the random sampling of both fasting and non-fasting males and females in an age group of 18 to 60, measurements of clot dot concentration had a smaller standard deviation (0.33) versus the plasma preparation measurements whose standard deviation was 0.52. Again the clot dot method is shown to be more precise and reproducible.

TABLE 2

Plasma Normal Range vs. "Clot Dot" Normal Range
Subjects: Male and female ages 18–60
Samples: Random - fasting and non-fasting

| | Plasma | "Clot Dot" |
|---|---|---|
| Number of Observations | 99 | 52 |
| Mean CM C (μ/ml) | 1.09 | 0.90 |
| Standard Deviation | 0.52 | 0.33 |
| Low Value | 0.34 | 0.36 |
| High Value | 3.09 | 1.80 |

The foregoing examples clearly demonstrate that by the practice of the invention Somatomedin-C can be accurately measured without undue influence occasioned by exogenous generation of Somatomedin-C after the collection of the blood sample. The method requires only simple collection of a small amount of test blood, immediately followed by absorption on filter paper or other absorbent media and drying at ambient temperature prior to incubation. From the foregoing, it will be apparent that specimens so collected can be assayed by a wide variety of methods, e.g., the radioimmunoassay, fluorescent immunoassay, enzyme immunoassay and the chemically modified bacteriophage assay.

I claim:

1. A method for determining levels of Somatomedin-C in biological fluid which comprises the steps of:
   (a) collecting a specimen of biological fluid having an unknown content of Somatomedin-C by absorption on an absorbent medium;
   (b) drying the absorbent medium;
   (c) eluting the Somatomedin-C activity from the absorbent medium; and
   (d) determining the Somatomedin-C activity of the eluate.

2. A method as claimed in claim 1 wherein the activity is eluted from a portion of the medium of predetermined size and dimension.

3. A method for suppressing exogenous generation of Somatomedin-C in biological fluid specimens, which comprises the steps of:
   (a) collecting a fluid specimen having an unknown content of Somatomedin-C;
   (b) absorbing the fluid on an absorbent medium;
   (c) drying the medium.

4. A method as claimed in claim 1 or 3 wherein the absorbent medium is filter paper.

5. A method as claimed in claim 1 or 3 wherein the drying of the medium is done at ambient temperature.

6. A method as claimed in claim 1 or 3 wherein the drying of the medium is done at room temperature.

7. A method as claimed in claim 1 or 3 wherein the biological fluid is a species of blood.

* * * * *